United States Patent [19]

Mackool

[11] Patent Number: 4,718,906
[45] Date of Patent: Jan. 12, 1988

[54] INTRAOCULAR LENS

[76] Inventor: Richard J. Mackool, 31-27 41st St., Astoria, N.Y. 11103

[21] Appl. No.: 838,545

[22] Filed: Mar. 11, 1986

[51] Int. Cl.⁴ .................................. A61F 2/16
[52] U.S. Cl. ........................................... 623/6
[58] Field of Search ................................ 623/6

[56] References Cited

U.S. PATENT DOCUMENTS

| Re. 31,963 | 8/1985 | Kelman | 623/6 |
|---|---|---|---|
| 3,711,870 | 1/1973 | Deitrick | 623/6 |
| 3,991,426 | 11/1976 | Flom et al. | 623/6 |
| 4,053,953 | 10/1977 | Flom et al. | 623/6 |
| 4,056,855 | 11/1977 | Kelman | 623/6 |
| 4,092,743 | 6/1978 | Kelman | 623/6 |
| 4,134,160 | 1/1979 | Bayers | 623/6 |
| 4,159,546 | 7/1979 | Shearing | 623/6 |
| 4,174,543 | 11/1979 | Kelman | 623/6 |
| 4,249,271 | 2/1981 | Poler | 623/6 |
| 4,249,272 | 2/1981 | Poler | 623/6 |
| 4,253,200 | 3/1981 | Kelman | 623/6 |
| 4,268,921 | 5/1981 | Kelman | 623/6 |
| 4,296,501 | 10/1981 | Kelman | 623/6 |
| 4,338,687 | 7/1982 | Rainin | 623/6 |
| 4,340,979 | 7/1982 | Kelman | 623/6 |
| 4,370,760 | 2/1983 | Kelman | 623/6 |
| 4,403,354 | 9/1983 | Rainin | 623/6 |
| 4,434,515 | 3/1984 | Poler | 623/6 |
| 4,435,050 | 3/1984 | Poler | 623/6 X |
| 4,439,873 | 4/1984 | Poler | 623/6 |
| 4,450,593 | 5/1984 | Poler | 623/6 |
| 4,451,938 | 6/1984 | Kelman | 623/6 |
| 4,477,931 | 10/1984 | Kelman | 623/6 |
| 4,495,665 | 1/1985 | Kelman | 623/6 |
| 4,524,468 | 6/1985 | Kelman | 623/6 |
| 4,567,546 | 4/1987 | Shearing | 623/6 |
| 4,573,998 | 3/1986 | Mazzocco | 623/6 |
| 4,605,409 | 8/1986 | Kelman | 623/6 |
| 4,608,049 | 8/1986 | Kelman | 623/6 |
| 4,615,702 | 10/1986 | Koziol et al. | 623/6 |

OTHER PUBLICATIONS

Thomas R. Mazzocco, "Implant Techniques: Small-Incision Insertion of the New Silicone and Silicone/Polyimide Intraocular Lenses," *Ocular Surgery News*, Dec. 15, 1985, pp. 26–27.

Primary Examiner—Ronald L. Frinks
Attorney, Agent, or Firm—Cobrin & Godsberg

[57] ABSTRACT

An intraocular lens consisting of a relatively soft plastic capable of being folded, and a harder plastic mounted on, or in, the relatively soft plastic, and wherein the relatively harder plastic resists folding when the soft plastic is folded, the lens further comprising one or more haptics attached to the harder plastic for retaining the lens in a selected location in the eye.

4 Claims, 11 Drawing Figures

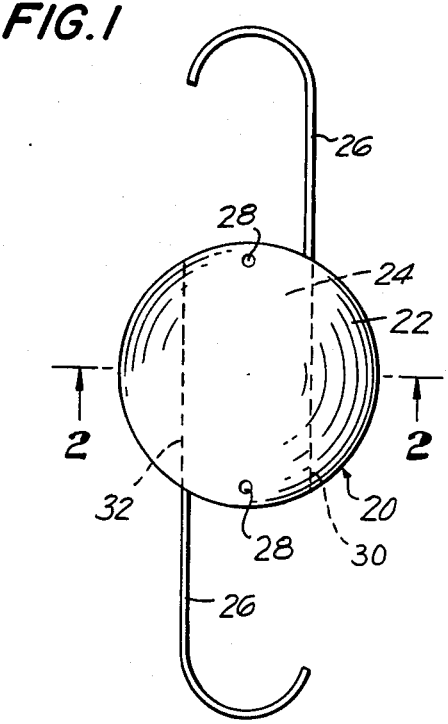
FIG. 1
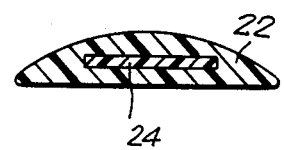
FIG. 2
FIG. 3
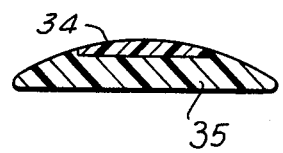
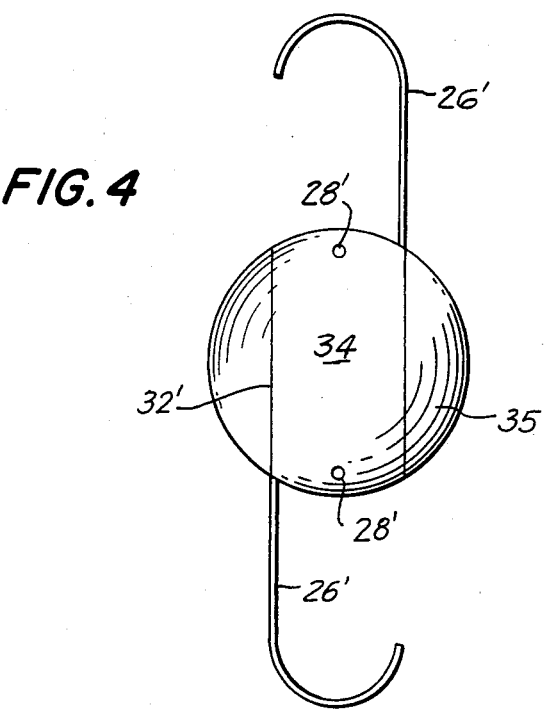
FIG. 4

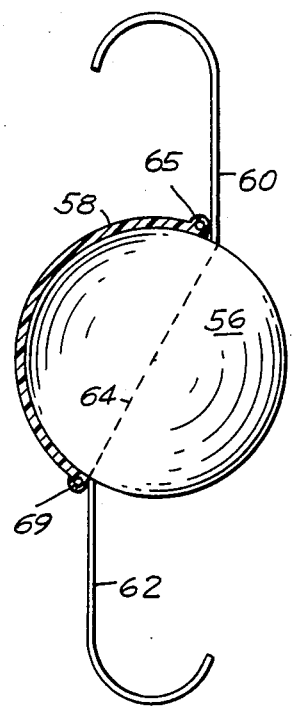
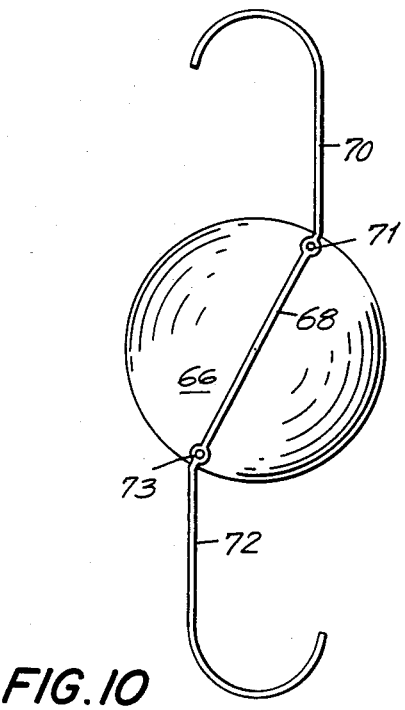
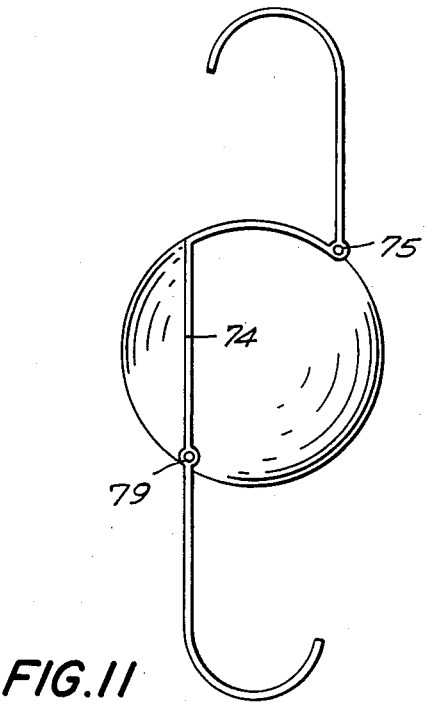

INTRAOCULAR LENS

BACKGROUND OF THE INVENTION

This invention relates to lenses, and more particularly to intraocular lenses.

The natural eye, in humans and most, if not all, animals, contains a lens located internally which focuses images on the retina. Either through disease or other naturally occurring processes, or mutations, the lens may fail to function properly. For instance, the lens, by mutation, may have been eliminated from the eye during its formation at birth. Or the lens may be cloudy at birth, or become cloudy over time. This clouding of the lens is known as a cataract, which inhibits the transmission of visual information through the lens to the retina.

The removal of diseased natural lenses has, prior to the advent of intraocular lenses, required a large incision into the eye at the junction of the cornea and the sclera in order to remove the lens. Healing time was substantial and pain was severe. No lens was inserted in place of the natural lens, and eyeglasses or external contact lenses were employed to help correct restored vision.

The advent of intraocular lenses, along with the instruments needed to insert them, was helpful. Incisions were still relatively large, on the order of 10-14 mm, and healing time remained substantial; however, this incision length was required for cataract removal, whereas intraocular lens implants required only a 6 or 7 mm incision for their insertion. More recently, cataract extraction by ultrasonic destruction and suction has been developed and allows the removal of the cataract through an incision of 3 mm. However, this incision must then be enlarged to 6 or 7 mm for insertion of the intraocular lens implant. Experience has shown that the longer the incision, the longer it takes to heal, the greater the danger of rupture of the incision postoperatively, and the greater the danger that scar tissue which forms during the healing process will interfere with vision. It is therefore desirable to develop an intraocular lens implant capable of being inserted through an incision not greater than that which is necessary for cataract extraction, i.e., 3 mm.

One proposal for reducing the length of the incision, which is the subject of a recently allowed patent of the inventor herein (Ser. No. 643,030, filed 8/21/84), involves making the intraocular lens in multiple parts. Each part is inserted through the reduced incision and then the individual parts are assembled together within the eye. The technique, while permitting the use of a relatively small incision, requires extra dexterity and handling by the surgeon of the multiple parts of the lens.

Another proposal for reducing the length of the incision requires the use of a very soft material for the lens, soft enough to permit the lens to be folded, inserted through the incision, and released. But the lens, which is made from silicone, is extremely soft. As a result, when the lens and its haptics are permitted to unfold in the eye, the almost jelly-like softness of the lens makes it difficult for the surgeon to position the lens in the eye essentially parallel to the plane of the iris. The jelly-like softness of the lens does not provide sufficient rigidity for the lens after insertion, and, as the lens moves about, the optical integrity of the lens may thereafter be affected. In addition, the jellylike softness of this lens makes it difficult to insert, unfold and position the lens via its haptics in the posterior chamber of the eye. It is the posterior chamber into which most intraocular lenses are placed as it is behind the iris, like the natural lens it replaces.

Furthermore, there is often a compressive force exerted on the lens by ocular structures following surgery, and these can and have resulted in deformation of the soft lens and reduced vision. One of these potentially compressing structures, the lens capsule, surrounds the human lens entirely. It is common practice for the lens implant to be intentionally placed within the capsule following the removal of the cloudy lens or cataract from within the capsule. This is widely accepted to be a preferred method for securing the lens implant as great stability is afforded the implant, and its position within the capsule prevents the implant from contacting more delicate ocular structures. Silicone lenses are, however, not recommended for this type of placement within the capsule as the compressive forces from the capsule can and have produced lens distortion and reduced vision following surgery. Nonetheless, it is not always possible for the surgeon to be certain that the lens implant in the posterior chamber has not been wholly or partially placed inadvertently within the capsule, or that it might shift into such a position postoperatively.

BRIEF DESCRIPTION OF THE INVENTION

The new intraocular lenses of the present invention continue the inexorable march to lenses that can be inserted through ever smaller incisions. The lenses of the present invention are made of a soft material capable of being folded for insertion through a small incision on the order of 3 mm. The lenses are, in addition, provided with a more rigid plastic over a portion of the lens, the relatively rigid plastic providing support for the lens during folding prior to insertion, and in the eye after insertion and unfolding. The relatively rigid plastic lends support to the entire lens structure after its insertion into the posterior chamber of the eye, and tends to help preserve the optical integrity of the lens after insertion and the closure of the incision.

Further, in accordance with the present invention, the edge of the intraocular lens may be made with one or more positioning indentations or holes. These indentations or holes accept the point of a small positioning tool and permit the surgeon to position or reposition the lens in the posterior chamber, thus helping the surgeon to best locate the lens for maximum benefit to the patient.

The intraocular lens of the present invention can take many different forms. In principle, the provision of a soft lens material capable of being easily folded, such as silicone or hydroxyethylmethacrylate (HEMA), or other acrylic material, and a rigidizing structure on, attached to, or in the lens, made from a relatively hard plastic such as polymethylmethacrylate (PMMA), form the basis of the invention. The soft plastic allows the lens to be folded and is optically acceptable. The hard plastic provides integrity and support for the lens during and after insertion, and is placed on, or attached to, or placed in the soft plastic in a manner which does not interfere with the foldability of the lens or unacceptably affect the optical characteristics of the lens. The hard plastic also determines the point or line on which the soft plastic will fold, and should be hard enough in relation to the soft plastic to resist folding to any substantial degree when the soft plastic is folded.

The hard plastic, in the event its placement may be located within or on the portion of the intraocular lens through which the patient will see (the "optic" of the lens), must be made of optical quality plastic. Although many plastics can serve this purpose—to provide relative rigidity and the capacity to be machined to provide optical correction—and can be used in the lenses of the invention, PMMA is the plastic of choice for the more rigid plastic.

The structures of the lenses of the present invention lend themselves to the use of haptics made from the same relatively rigid plastic material and other rigid plastic materials, such as polypropylene, which are currently favored as haptic material for lens implants. As a result, the surgeon will have less difficulty positioning the lens, and the extra support provided by the stiffer haptics tends to help retain the lens in place. Compression and distortion of the soft plastic optic by the lens capsule or other ocular structures will therefore not occur, and optical integrity is thus insured after closure of the incision.

BRIEF DESCRIPTION OF THE DRAWINGS

Referring now to the drawings in which several embodiments of the invention are illustrated, and in which like numerals refer to like parts:

FIG. 1 is a top plan view of an intraocular lens in accordance with the present invention;

FIG. 2 is a sectional view of the lens of FIG. 1 taken along line 2—2;

FIG. 3 is a sectional view of another embodiment of the lens illustrating the placement of the harder plastic in a different manner;

FIG. 4 is a top plan view of FIG. 3;

FIG. 9 is a further embodiment of the invention showing a different placement of the hard plastic material;

FIG. 10 is a plan view of still another embodiment of the invention showing the use of a thin band or bar of hard plastic material; and FIG. 11 is a plan view of a still further embodiment of the invention.

DESCRIPTION OF THE PREFERRED EMBODIMENTS

Figure 5:
FIG. 5 is a cross-sectional view of another embodiment of the invention.

Referring to FIG. 1, an embodiment of an intraocular lens in accordance with the present invention is illustrated. The numeral 20 denotes a lens "optic" which is about 6 mm in diameter. The 6 mm diameter is fairly standard in the art, and is generally chosen to cover the pupil in its fully dilated state under natural occurring conditions.

The numeral 22 denotes the soft plastic portion of the lens, which, in this instance, is the entire surface of the lens. Numeral 24 is the portion of the lens made of the more rigid plastic, 26 denotes the haptics, and the numeral 28 denotes the positioning indentations or openings for use by the surgeon in positioning the lens after its insertion through the incision into the eye (not shown).

The diameter of the intraocular lens illustrated in FIG. 2 is 6 mm. The width of the central hard plastic portion of the lens is 3 mm, or one-half the diameter of the lens. The haptics are mounted to the edges of the hard plastic lens along the lines which constitute the demarcation line between the hard and soft plastic portions of the lens. As stated above, the haptics are made of a harder plastic, in comparison to the soft plastic of the lens, and preferably of the same material as that used for the relatively harder portion of the lens. However, it should be understood that any plastic medically acceptable for implantation can be used as long as the rigidity of the material is sufficient to help anchor the lens to which it is attached in the posterior chamber of the eye.

The lens of FIG. 1 may be folded prior to insertion by small, thin forceps of the type presently in use by ophthalmic surgeons. Folding using the forceps occurs along demarcation lines 30, 32, with the soft plastic folding over the relatively harder plastic portion 24. By mounting the haptics 26 along the demarcation lines, when the lens is folded for insertion, the haptics remain within the envelope defined by the cross-section of the folded lens.

Insertion of the folded lens is led by one haptic, which is presented to the incision. As the haptic moves into and through the incision, the folded body of the lens follows, trailed by the second haptic. Because of the geometry of the lens of FIG. 1, its insertion is along a plane. As a result, the lens is easier to handle and easier to locate in the targeted location within the posterior chamber of the eye.

After the lens is in the targeted location, it is released to unfold. Because the unfolding material is soft, and further because the haptics do not also unfold or whip about in the eye during the unfolding process, the potential for damage to the interior tissue of the eye in the vicinity of the inserted lens is substantially lessened, if not eliminated.

After the lens is unfolded, the forceps are extracted by the surgeon through the incision and a tool to engage the positioning indentations or openings 28 is then inserted to move the lens in the posterior chamber until it is finally located in accordance with the surgeon's wishes.

FIG. 2 illustrates the manner of assembly of the hard and soft plastic in the embodiment of FIG. 1. In this instance, the hard plastic is embedded within the soft plastic. This structure can be achieved by concurrent extrusion of the two plastics, or by solidifying the soft plastic about the harder plastic. Both techniques, as well as other techniques for embedding one plastic in another, are well known to those of ordinary skill in the plastics art.

FIGS. 3 and 4 are another embodiment of the invention in which the soft plastic of the lens of FIG. 1 is chiselled out to receive a hard plastic insert 34, which may then be fused to the soft plastic 35 by conventional techniques. FIG. 3 illustrates the depth to which the hard plastic is inserted, and can extend through the full thickness of the lens.

Figure 6:
FIG. 6 is a sectional view of a still further embodiment of the invention showing still another, low-depth configuration of the hard plastic.
Figure 7:
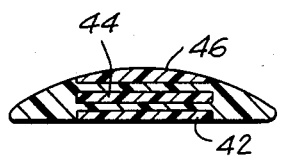
FIGS. 7 and 8 are sectional views of still other embodiments of the invention illustrating still other placements of the invention.
Figure 8:
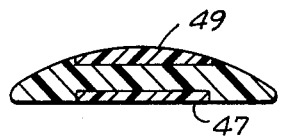

There are many configurations in which the hard and soft plastics are combined to provide foldability for insertion through a small incision and enough rigidity to preserve optical integrity once the lens has been inserted and the incision closed. A few additional illustrations are provided in FIGS. 5, 6, 7 and 8. FIGS. 5 and 6 are cross-sectional views of the positioning of the hard plastic 36 and 37, respectively, in the the soft plastic, and FIG. 7 which illustrates multiple hard plastic bands 42, 44 and 46 for the purpose, and FIG. 8, which illustrates two hard plastic bands 47 and 49. In each, the use of haptics made of a relatively harder material than the soft plastic is contemplated, all as more fully described in connection with FIG. 1.

In each of the above embodiments, the diameter of the lens is approximately 6 mm in accordance with good intraocular lens making practice. For best results, the hard plastic section or portion of the lens should not exceed 3 mm in width, although smaller widths can be used.

FIG. 9 illustrates still another embodiment of the invention. In this particular embodiment, the soft plastic 56 comprises essentially the entire lens. The hard plastic 58 is fused to the edge of the lens and extends approximately 180° along the lens circumference. Haptics 60, 62 are attached to the ends of the hard plastic edge by conventional techniques, such as fusion.

When the lens is folded for insertion, it folds on a line defined by the ends of the hard edges shown in dotted outline and denoted by the numeral 64, to about half the original 6 mm size of the lens. Insertion is achieved by using the techniques described above, also employing positioning holes or indentations 65 and 69 which are placed in the hard plastic. Placing the positioning holes in the soft plastic might cause the soft plastic to tear.

In the various embodiments shown, two or more positioning indentations or holes are shown. For purposes of this invention, one or more indentations or holes can be employed, as desired, provided the use of extra positioning holes or indentations does not interfere with the optical or structural integrity of the lens. The positioning holes are generally placed in the hard plastic material which allows maximum control over implant positioning.

FIG. 10 illustrates still another embodiment of the invention in which the entire lens is made of soft plastic material 66. The harder plastic is a thin line of material embedded or fused to one surface of the lens, here denoted by the numeral 68, to which the haptics 70, 72 are affixed by fusion or another conventional plastic joining technique. The lens folds about the hard plastic band 6 to about half its size for insertion using the techniques first described above. Numerals 71 and 73 denote two positioning holes or indentations that are on the hard plastic and may be placed either within the optic, or outside the optic and within the haptic sections of the implant.

FIG. 11 illustrates still another embodiment of the invention, similar to FIG. 10, in which the hard plastic band 74 crosses the lens surface offset from the center of the lens. The hard plastic further continues along the edge of the lens at opposed locations. But the lineal extent of the hard plastic bar along the edges is not more than 180°, or half the circumference of the lens, to permit the greatest degree of foldability. Numerals 75 and 79 refer, again, to positioning holes or indentations.

The embodiments above are intended to be illustrative of the invention only, and it is expected that those of ordinary skill in the art may, in view of the teachings contained hereinabove, be able to modify the embodiments illustrated herein. It is intended to cover all such modifications which fall within the spirit and scope of the invention as defined by the claims appended hereto.

What is claimed is:

1. A plastic intraocular lens capable of being inserted into an eye through an incision which is smaller than the diameter of the lens comprising a first plastic capable of being folded by an ophthalmic surgeon during the process of inserting the intraocular lens during eye surgery, a second plastic harder than the first plastic capable of resisting folding when the first plastic is folded; the second plastic forming a thin bar across a part of the surface of the first plastic; one or more haptics connected to the second plastic; and positioning means on the second plastic to permit the positioning of the intraocular lens in the eye after insertion by the surgeon.

2. The intraocular lens according to claim 1 in which the second plastic is located in the edge of the first plastic and extends along approximately 180° of the aforesaid edge.

3. The intraocular lens according to claim 1 in which the second plastic crosses the diameter of the first plastic.

4. A plastic intraocular lens capable of being inserted into an eye through an incision smaller than the unfolded diameter of the intraocular lens comprising a first plastic capable of being folded by an opthalmic surgeon during the process of inserting the intraocular lens during eye surgery; a second plastic harder than the first plastic, located on or in the first plastic capable of resisting folding when the first plastic is folded; haptics attached to the second plastic for retaining the intraocular lens in the eye after its insertion; the second plastic having positioning means to move the intraocular lens within the eye to a selected, targeted location; the first plastic being grooved across its surface and the second plastic is located in said groove, with more than one band of said second plastic being located in said first plastic, each band being vertically spaced from the other band.

* * * * *